United States Patent
Ohki et al.

[11] 4,006,133
[45] Feb. 1, 1977

[54] AMINOGLYCOSIDE ANTIBIOTICS

[75] Inventors: Eiji Ohki, Ichikawa; Hiromichi Saeki, Yamato; Shinichi Sugawara, Tokyo, all of Japan

[73] Assignee: Sankyo Company Limited, Japan

[22] Filed: Oct. 18, 1974

[21] Appl. No.: 515,814

[30] Foreign Application Priority Data
Oct. 25, 1973   Japan .............................. 48-120325

[52] U.S. Cl. .................................. 536/17; 424/180
[51] Int. Cl.² ......................................... C07G 11/00
[58] Field of Search ............................. 260/210 AB

[56] References Cited
UNITED STATES PATENTS

| 3,784,541 | 1/1974 | Culbertson et al. | 260/210 AB |
| 3,826,802 | 7/1974 | Kawaguchi et al. | 260/210 AB |

OTHER PUBLICATIONS
Culbertson, T. P. "5''-Amino-deoxybutirosin-", J. of Antibiotics, vol. 26, No. 26, 1973, pp. 790–792.

Primary Examiner—Lewis Gotts
Assistant Examiner—Cary Owens
Attorney, Agent, or Firm—Toren, McGeady and Stanger

[57] ABSTRACT
New derivatives of the antibiotic butirosin A having the formula:

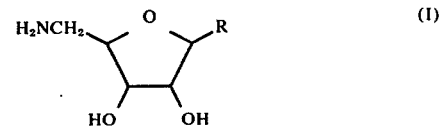

in which R is a radical of formula (II):

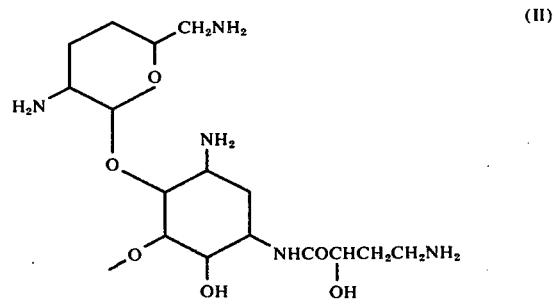

and pharmaceutically acceptable acid addition salts thereof.

The butirosin A derivatives of formula (I) can be prepared by reduction of a 5''-azido compound having the formula (III):

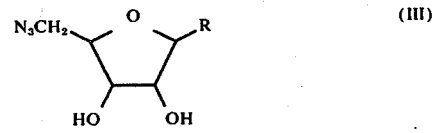

in which R' is the same groups R or a group which, on reduction, gives a group of formula (II).

The butirosin A derivatives of general formula (I) and pharmaceutically acceptable acid addition salts thereof are active against a broad spectrum of Gram-positive and Gram-negative bacteria, including some butirosin-resistant strains.

5 Claims, No Drawings

AMINOGLYCOSIDE ANTIBIOTICS

The present invention relates to new aminoglycoside antibiotics and, more particularly, to new derivatives of the antibiotic butirosin A.

The invention provides, as new compounds, derivatives of butirosin A having the formula:

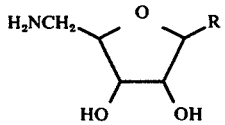

in which R represents a group having the formula (II):

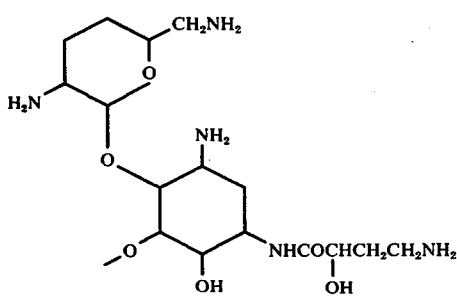

and pharmaceutically acceptable acid addition salts thereof.

The butirosin A derivatives of formula (I) can be prepared by reduction of a 5''-azido compound having the formula (III):

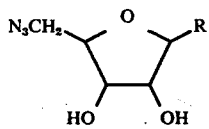

in which R' is the same group as R or a group which, on reduction, gives a group of formula (II). If the group R' in the compound of formula (III) is a group which may be converted by reduction to a group of formula (II), reduction of the 5''-azido group in the compound of formula (III) yields a compound of formula (I) in which R is a group of formula (II).

An example of a group which can be reduced to give a group of formula (II) is a group of general formula (IV):

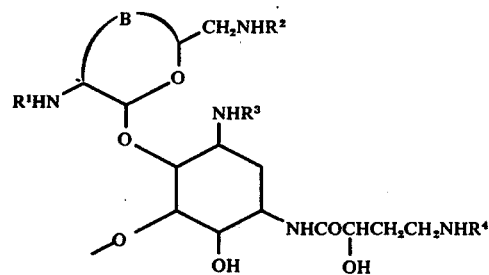

wherein: $R^1$, $R^2$, $R^3$ and $R^4$ may be the same or different and each represents a group removable by catalytic reduction to leave a free amino group in the product; and B represents a group having the formula —$CH_2$—$CH_2$— or —CH=CH—. Groups removable by catalytic reduction, so as to leave a free amino group in the product of formula (I) include: aralkoxycarbonyl groups, particularly arylmethoxycarbonyl groups, such as the benzyloxycarbonyl group or substituted benzyloxycarbonyl groups, e.g. p-nitrobenzyloxycarbonyl, p-methoxybenzyloxycarbonyl, trichlorobenzyloxycarbonyl, benzhydryloxycarbonyl or naphthylmethoxycarbonyl; and the allyloxycarbonyl group.

The preferred compounds of formula (III), which may be used as starting materials for the preparation of the compounds of the present invention are those having the general formula (V):

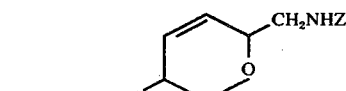
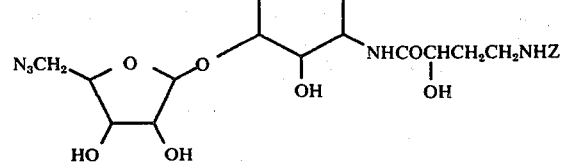

in which Z is the benzyloxycarbonyl group or a substituted benzyloxycarbonyl group, such as those exemplified above.

The reduction can be carried out using any conventional reduction process which is capable of reducing an azido group to an amino group and which, where required, is capable of removing the groups $R^1$, $R^2$, $R^3$ and $R^4$ to leave free amino groups and/or of saturating a double bond. The reduction is most conveniently a catalytic reduction process, in which the compound of formula (III) is contacted with hydrogen in the presence of a catalyst, and normally in an appropriate solvent. The choice of solvent is not critical, provided that it does not interfere with the reaction. Suitable solvents include: water; alcohols, such as methanol, ethanol and isopropanol; ethers, such as dioxane and tetrahydrofuran; dimethylformamide; and mixtures thereof. An aqueous alcohol is particularly preferred. If the starting material is a compound of formula (III) wherein any of $R^1$, $R^2$, $R^3$ and $R^4$ represents an aralkoxycarbonyl group, the reaction tends to proceed more smoothly if performed in the presence of an acid, such as hydrochloric acid, hydrobromic acid, or trifluoroacetic acid. The catalyst may be any of those conventionally employed for the saturation of a double bond and the removal of said protective group: for example, metals such as palladium, platinum, nickel and rhodium, the oxides of these metals, and these metals supported on carriers such as carbon, barium carbonate, barium sulphate and silk yarn. It is generally preferred to use palladium on carbon as the catalyst. The reaction is conveniently performed at room temperature and atmospheric pressure, but other temperatures and pressures may also be used. It generally takes from a few minutes to a few hours to complete the reaction.

After completion of the reaction, the desired product can be recovered from the reaction mixture by conventional techniques: for example, the catalyst is filtered off, the filtrate is treated with a weakly basic anion exchange resin so as to adjust its pH to approximate neutrality, the resin is then filtered off, and the solvent is distilled from the filtrate, giving the desired product. If desired, the product can be purified by conventional methods, such as ion exchange chromatography.

The acid addition salts of the invention can be prepared in the conventional manner, by the salification of the compound of formula (I) with an appropriate inorganic or organic acid, for example hydrochloric, hydrobromic, sulphuric, phosphoric, carbonic, acetic, succinic, citric, maleic or malic acid. The carbonate is the particularly preferred acid addition salt.

The compounds of formula (III) are themselves new and may be prepared from butirosin A, which has the formula (VI) by the method illustrated in the following reaction scheme with reference to the preparation of a compound of formula (V). In the formulae of the reaction scheme, Z is as previously defined; $R^5$ represents an alkanoyl or substituted or unsubstituted benzoyl group, e.g. an acetyl, propionyl or benzoyl group; $R^6$ represents an alkylsulphonyl group, such as a mesyl group; and $R^7$ represents a benzenesulphonyl group or substituted benzenesulphonyl group, e.g. a tosyl or trimethylbenzenesulphonyl group.

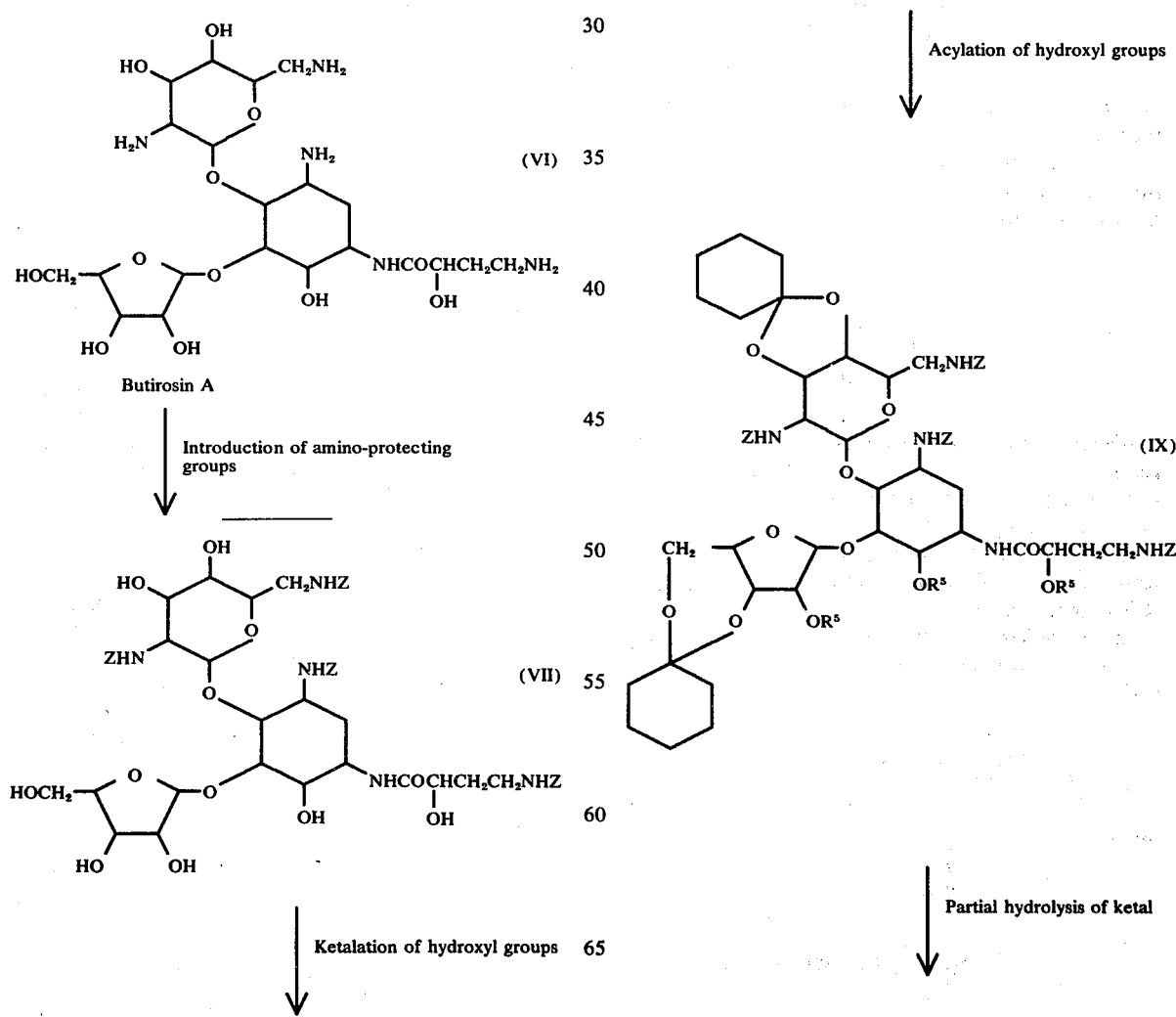

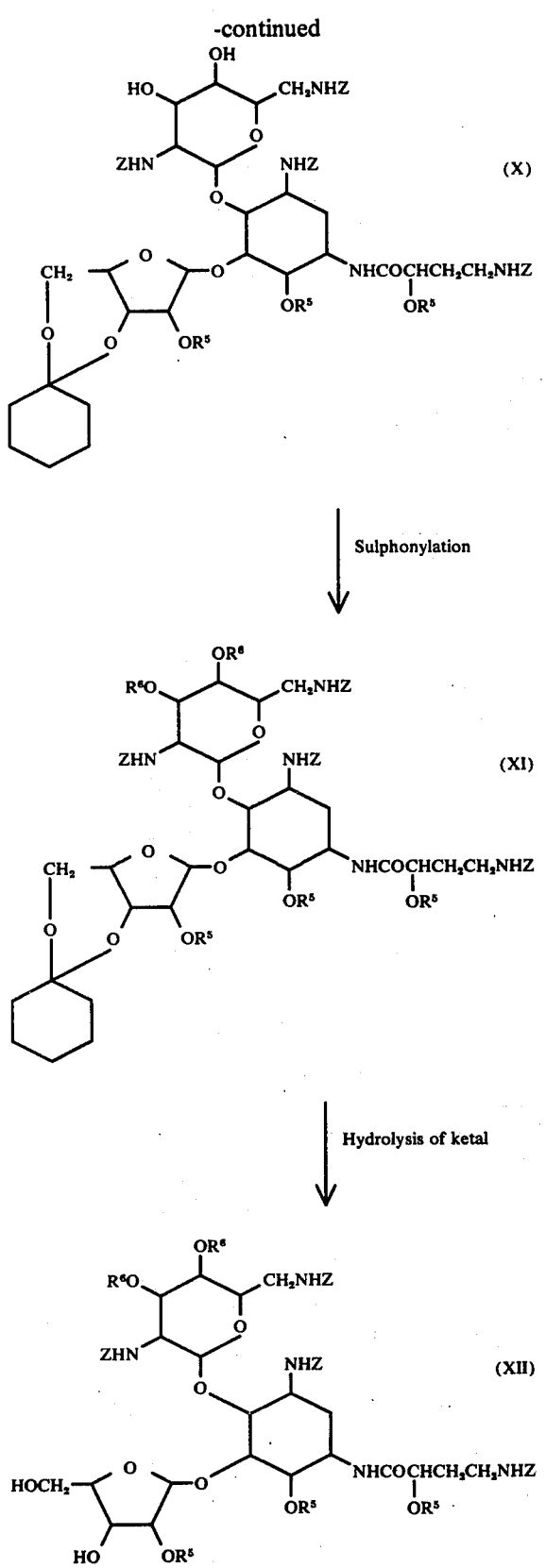
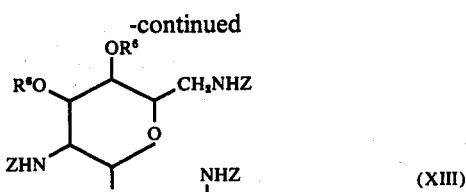

It has surprisingly been discovered that the butirosin A derivatives of general formula (I) and pharmaceutically acceptable acid addition salts thereof are active against a broad spectrum of Gram-positive and Gram-negative bacteria, including some butirosin-resistant strains and, since their antibacterial activity is generally greater than that of butirosin A, they can be administered in smaller doses than butirosin A whilst still achieving the same effect.

The antibacterial activity of 5''-amino-3',4',5''-trideoxybutirosin A (ATBA), a compound of formula (I) in which the group R is of formula (II), is compared with that of butirosin A (BA) in the following Table, which shows the minimum inhibitory concentration of the two compounds with respect to different micro-organisms. The minimum inhibitory concentration values were measured in Hurt's infusion agar and are expressed in micrograms per millilitre. It will be seen from the Table that ATBA is extremely active against butirosin-resistant as well as butirosin-sensitive strains.

Table

| Micro-organism | Minimum inhibitory concentration | |
| --- | --- | --- |
| | ATBA | BA |
| *Bacillus anthracis* | 0.1 | 0.8 |
| *Bacillus subtilis* PCl-219 | 0.1 | 0.4 |
| *Staphylococcus aureus* 209 P | 0.2 | 1.5 |

Table -continued

| Micro-organism | Minimum inhibitory concentration | |
|---|---|---|
| | ATBA | BA |
| Staphylococcus aureus 109 | 3.1 | >200 |
| Staphylococcus aureus 126 | 1.5 | 6.5 |
| Staphylococcus aureus 163 | 25 | >200 |
| Staphylococcus aureus 167 | 0.1 | 200 |
| Staphylococcus epidermidis | 1.5 | 0.4 |
| Escherichia coli NIHJ | 3.1 | 3.1 |
| Escherichia coli 605 | 25 | >200 |
| Escherichia coli 620 | 12.5 | >200 |
| Escherichia coli 665 | 12.5 | >200 |
| Escherichia coli 704 | 6.2 | 12.5 |
| Klebsiella 806 | 6.2 | 3.1 |
| Klebsiella 813 | 25 | 50 |
| Salmonella enteritidis | 6.2 | 12.5 |
| Salmonella typhi-murium | 6.2 | 12.5 |
| Shigella flexneri 2a | 3.1 | 6.2 |
| Shigella sonnei | 3.1 | 6.2 |
| Proteus mirabilis 1306 | 25 | 50 |
| Proteus mirabilis 1312 | 50 | 100 |
| Proteus vulgaris 1404 | 6.2 | 25 |
| Proteus vulgaris 1416 | 50 | 100 |
| Proteus morganii 1501 | 1.5 | 3.1 |
| Proteus morganii 1512 | 3.1 | 25 |
| Proteus rettgeri 1601 | 1.5 | 6.2 |
| Proteus rettgeri 1602 | 12.5 | >200 |
| Pseudomonas aeruginosa Scr. | 1.5 | 12.5 |
| Pseudomonas aeruginosa 1016 | 3.1 | >200 |
| Pseudomonas aeruginosa 1055 | 6.2 | >200 |
| Pseudomonas aeruginosa 1080 | 100 | >200 |
| Pseudomonas aeruginosa 1100 | 25 | >200 |
| Pseudomonas schuylkilliensis | 6.2 | 25 |

By virtue of these properties, the compounds of formula (I) and their pharmaceutically acceptable acid addition salts are valuable pharmaceutically as antimicrobial agents. Accordingly, the invention provides a pharmaceutical composition comprising a compound of formula (I) or a pharmaceutically acceptable acid addition salt thereof and a pharmaceutical carrier or diluent.

The compounds of the present invention can be formulated in the conventional manner with the usual pharmaceutical carriers and diluents, and with appropriate pharmaceutical adjuvants, to produce compositions of the desired type. As with previously known aminoglycoside antibiotics, parenteral administration is preferred, for example by intravenous, intramuscular or subcutaneous injection, and the pharmaceutical compositions of the invention will, therefore, most commonly be formulated for administration by these routes. However, compositions for oral administration, such as capsules, tablets, granules and syrups, can also be employed. Compositions in unit dosage form are normally preferred. The posology will depend on the clinical details of the case under treatment, but the total daily dose for adults will normally be from 10 to 1,000 mg, more usually from 50 to 200 mg, conveniently administered in divided doses 2–4 times per day.

The following Example illustrates the preparation of a butirosin A derivative in accordance with the invention.

EXAMPLE

5''-Amino-3',4',5''-trideoxybutirosin A carbonate 685 mg of 5''-azido-tetra-N-benzyloxycarbonyl-3',4',5''-trideoxy-3'-enobutirosin A were dissolved in a mixture of 30 ml of methanol, 10 ml of water and 2 ml of 2N hydrochloric acid. 2.5 g of 10% palladium on carbon were added, and hydrogen was introduced into the resulting mixture for 2 hours, with stirring, at room temperature. Water was then added to the reaction mixture, and the mixture was filtered. The pH of the filtrate was adjusted to neutral by the addition of Amberlite IR-45 ion exchange resin in the OH⁻ form (AMBERLITE is a Trade Mark). The ion exchange resin was filtered off, and the methanol was distilled off from the filtrate under reduced pressure. The residual aqueous solution was passed through a column packed with 50 ml of Amberlite CG-50 ion exchange resin in the $NH_4^+$ form (AMBERLITE is a Trade Mark) to adsorb the desired product from the solution. The column was eluted successively with 0.3N, 1N and 1.5N aqueous ammonia. Ninhydrin-positive portions of the eluate with 1N and 1.5N ammonia were separated and identified by thin-layer chromatography, developed with a mixture of methanol and concentrated aqueous ammonia in equal parts by volume. The portions giving a single spot on the chromatogram corresponding to the desired product were collected and concentrated, solid carbon dioxide was added, the concentrated liquid was filtered, and the filtrate was lyophilized, giving 140 mg of the desired product in the form of a powder.

The product began to soften at about 140° C, and melted at about 175° C with liberation of gaseous carbon dioxide.

$[\alpha]_D^{21} = +12.8°$ (C = 1.09, $H_2O$)

Elemental analysis: Calc. for $C_{21}H_{42}N_6O_9 \cdot 2\frac{1}{2}H_2CO_3 \cdot H_2O$: C, 40.57%; H, 7.10%; N, 12.08%; Found: C, 40.23%; H, 6.88%; N, 11.97%.

The preparation of the novel starting materials used in the process of the invention is illustrated below, with reference to the compound 5''-azido-tetra-N-benzyloxycarbonyl-3',4',5''-trideoxy-3'-enobutirosin A which is used as the starting material in the foregoing Example.

(1) Tetra-N-benzyloxycarbonylbutirosin ("Compound A")

11.7 g of butirosin disulphate dihydrate (comprising a mixture of butirosins A and B in the ratio of 4:1) were dissolved in a mixture of 200 ml of water and 80 ml of methanol, and 8.0 g of anhydrous sodium carbonate were added to the resulting solution. 10.5 ml of benzyloxycarbonyl chloride were added dropwise to the mixture over a period of 30 minutes, with vigorous stirring and under ice-cooling, and then 20 ml of methanol were added. The resulting mixture was stirred for a further 3 hours at room temperature, then the methanol was distilled off under reduced pressure and at a bath temperature of below 45° C. Ice-cold water was added to the residue, whereupon an oily layer separated out and the aqueous layer was decanted off. The oil was washed with ice-cold water, again allowed to separate out, and the aqueous layer was decanted off. This operation was repeated with water, and then twice with 50 ml portions of diethyl ether.

The oil thus obtained was dissolved in methanol, and the solution was filtered. The methanol was distilled off from the filtrate, under reduced pressure. 300 ml of diethyl ether were added to the residue, and the resulting mixture was allowed to stand overnight in a refrigerator. The upper layer was then decanted off, and all the solvent was removed from the residue under reduced pressure, giving 17.7 g of crude "Compound A" in the form of a colourless powder. This product was suitable for use in the next stage of the process, without further purification.

In order to prepare a pure sample for analysis, a portion of the crude product was dissolved in dioxane, and the solution was passed through a column packed with 20 times the solution volume of silica gel. The adsorbed product was eluted from the column with chloroform containing 5-15% by volume of methanol. The solvent was distilled off from the eluate under reduced pressure, and the residue was dissolved in a small volume of methanol. Diethyl ether was added to the solution, thereby precipitating the pure Compound A in the form of a powder.

IR spectrum in Nujol (Trade Mark): $\nu =$
  1700 (broad strong absorption due to carbonyl of benzyloxycarbonyl),
  1540 (strong absorption due to amide II), cm$^{-1}$.
$[\alpha]_D^{27} = + 16.6°$ (C = 1.85, CHCl$_3$)

Elemental analysis: Calculated for C$_{53}$H$_{65}$N$_5$O$_{20}$: C, 58.29%; H, 6.00%; N, 6.41%; Found: C, 58.67%, H, 6.14%; N, 6.42%.

(2)
Tetra-N-benzyloxycarbonyl-3′,4′:3″,5″-di-O-cyclohexylidenebutirosin A ("Compound B")

10 g of the crude Compound A, obtained in the previous stage, were dissolved in 30 ml of anhydrous dimethylformamide; 6 ml of 1,1-dimethoxycyclohexane and 0.35 g of p-toluenesulphonic acid monohydrate were added to the solution; and the resulting mixture was stirred under reflux for 75 minutes, under reduced pressure, at a bath temperature of 35° C. An excess of anhydrous potassium carbonate was then added to the reaction mixture, which was then stirred for 20 minutes and filtered. The solvent was distilled off from the filtrate under reduced pressure and at a bath temperature of 50° C. The residue, dissolved in chloroform, was adsorbed on a column of 200 g of silica gel, from which it was eluted with chloroform containing 2-5% by volume of methanol. The presence of the product in the eluate was confirmed by thin-layer chromatography. The solvent was removed from the eluate, giving 6.5 g of the desired "Compound B" in the form of a powder. NMR spectrum (60 MHz, CDCl$_3$): $\zeta = 1.0 - 2.0$ (broad band, 10H, cyclohexylidene protons).
$[\alpha]_D^{27} = + 11°$ (C = 1.4, CHCl$_3$).

Elemental analysis: Calculated for C$_{65}$H$_{81}$N$_5$O$_{20}$: C, 62.34%; H, 6.52%; N, 5.59%; Found: C, 61.99%; H, 6.49%; N, 5.31%.

When the product was hydrolyzed with hydrochloric acid and then tested for the presence of sugars by means of paper chromatography using two developing solvent system, only xylose was detected. [Chromatography conditions: Toyo Roshi No. 51 filter paper, developing solvent A: upper layer of a mixture of ethyl acetate/pyridine/water (8:2:1) and developing solvent B: upper layer of a mixture of ethyl acetate/pyridine/water (3.6:1:1.15), detected by coloration with aniline hydrogen phthalate].

(3)
Tri-O-acetyl-tetra-N-benzyloxycarbonyl-3′,4′:3″,5″-di-O-cyclohexylidenebutirosin A ("Compound C")

3.7 g of Compound B, obtained in the previous stage, were dissolved in 20 ml of pyridine, 8 ml of acetic anhydride were added, and the resulting mixture was allowed to stand overnight at room temperature. The reaction mixture was then poured into ice-cold water, stirred vigorously, and allowed to stand for 30 minutes. The supernatant was decanted off, and the oily residue was dissolved in chloroform. The chloroform solution was washed successively with 2N hydrochloric acid, water, saturated aqueous sodium bicarbonate solution and again water, and then dried over anhydrous magnesium sulphate. The solvent was removed, leaving the desired "Compound C".
$[\alpha]_D^{27} = + 7.8°$ (C = 2.8, CHCl$_3$)

Elemental analysis: Calculated for C$_{71}$H$_{87}$N$_5$O$_{23}$: C, 61.86%; H, 6.39%; N, 5.08%; Found: C, 61.27%; H, 6.34%; N, 4.99%.

(4)
Tri-O-acetyl-tetra-N-benzyloxycarbonyl-3″,5″-O-cyclohexylidene-3′,4′-di-O-methanesulphonylbutirosin A ("Compound E")

4.29 g of Compound C, obtained in the previous stage, were dissolved in 40 ml of acetic acid, 12 ml of water were added to the solution, and the resulting mixture was allowed to stand for 2 hours at room temperature. A quantity of 1N aqueous sodium hydroxide solution sufficient to neutralize half the acetic acid in the mixture was then added, under ice-cooling, and the reaction mixture was extracted with chloroform. The chloroform extract was washed with cooled 1N aqueous sodium hydroxide solution until free from acetic acid, then with water, and dried over anhydrous magnesium sulphate. The solvent was distilled off, giving 3.6 g of crude tri-O-acetyl-tetra-N-benzyloxycarbonyl-3″,5″-O-cyclohexylidenebutirosin A ("Compound D").

The crude Compound D thus obtained was dissolved in 30 ml of pyridine, 7.2 ml of methanesulphonyl chloride were added, and the solution was allowed to stand for 1 hour at room temperature. The excess methanesulphonyl chloride was decomposed by adding a small amount of water to the reaction mixture, the mixture was then immediately neutralized by the addition of saturated aqueous sodium bicarbonate solution, and ice-cold water was added to complete the precipitation which occurred. The supernatant liquid was decanted off and reserved. The residue was washed with water, and then dissolved in chloroform. The washings from the residue were combined with the reserved supernatant, and the whole was extracted with a small amount of chloroform. The chloroform extract was combined with the chloroform solution of the residue, and the whole was washed successively with 2N hydrochloric acid, water, saturated aqueous sodium bicarbonate solution and again water. The chloroform solution was then dried over anhydrous magnesium sulphate, and the solvent was distilled off, giving 3.6 g of crude "Compound E" in the form of a yellow powder.

This crude product, dissolved in chloroform, was adsorbed onto a column of 72 g of silica gel, from which it was eluted with chloroform containing 1-2% by volume of methanol. The solvent was distilled off from the eluate, giving 2.6 g of the pure Compound E in the form of a colourless powder.

NMR spectrum (60 MHz, CDCl$_3$): $\delta = 3.07$ (s, methyl of one methane sulphonate), 2.81 (s, methyl of one methane sulphonate);
  2.13 (s, methyl of one acetyl);
  2.06 (s, methyl of two acetyls).
$[\alpha]_D^{27} = -14.3°$ (C = 1.5, CHCl$_3$).

Elemental analysis: Calculated for $C_{67}H_{83}O_{27}N_5S_2$: C, 55.32%; H, 5.75%; N, 4.82%; S, 4.41%. Found: C, 55.41%; H, 5.80%; N, 4.80%; S, 4.40%.

(5)
6,2',2'''-Tri-O-acetyl-tetra-N-benzyloxycarbonyl-3',-4'-di-O-mesylbutirosin A ("Compound F")

One gram of Compound E, obtained in the previous stage, was dissolved in a mixture of 10 ml of acetic acid and 4 ml of water, and the resulting solution was heated for 10 minutes over a boiling waterbath. The reaction mixture was then concentrated under reduced pressure, at a temperature below 50° C, and the concentrate was adsorbed on a column of 15 g of silica gel. The column was eluted with chloroform containing 2% by volume of methanol, and the solvent was distilled off from the eluate, giving 0.8 g of the desired Compound F in the form of a colourless powder.
$[\alpha]_D^{25} = +4.5°$ (C = 2.4, CHCl$_3$).
Elemental analysis: Calculated for $C_{61}H_{75}O_{27}N_5S_2$: C, 53.30%; H, 5.50%; N, 5.10%; S, 4.67%; Found: C, 53.14%; H, 5.48%; N, 5.22%; S, 4.24%.

(6)
6,2'',2'''-Tri-O-acetyl-tetra-N-benzyloxycarbonyl-3',-4'-di-O-mesyl-5''-O-tosylbutirosin A ("Compound G")

One gram of Compound F was dissolved in 4 ml of anhydrous pyridine, 0.5 g of tosyl chloride was added to the solution at a temperature of 0°–5° C, and the solution was then stirred for 2 hours at 20°–25° C. The reaction mixture was poured into ice-cold water and extracted with chloroform. The extract was washed successively with dilute hydrochloric acid, water, dilute aqueous sodium bicarbonate solution and again water. The solvent was distilled off from the extract, giving 1.1 g of crude "Compound G".

The crude product was adsorbed on a column of 20 g of silica gel, from which it was eluted with chloroform. Removal of the solvent from separate fractions of the eluate yielded, respectively, 144 mg of the 3'',5''-ditosyl compound and 660 mg of the pure desired "Compound G" in the form of a colourless powder. The pure Compound G had the following properties:
Melting point: 94°–105° C.
$[\alpha]_D^{25} = -4.3°$ (C = 1.25, CHCl$_3$).
NMR spectrum (60MHZ, CDCl$_3$) : δ =
3.10 (s, methyl of one methane sulphonate)
2.75 (s, methyl of one methane sulphonate)
2.43 (s, methyl of p-toluenesulphonate)
2.13 (s, methyl of two acetyls)
2.05 (s, methyl of one acetyl)
Elemental analysis: Calculated for $C_{68}H_{81}O_{29}N_5S_3$: C, 53.43%; H, 5.34%; N, 4.58%; S, 6.29%; Found: C, 53.67%; H, 5.34%; N, 4.60%; S, 6.10%.

(7)
6,2'',2'''-Tri-O-acetyl-5''-azido-tetra-N-benzyloxycarbonyl-5''-deoxy-3',4'-di-O-mesylbutirosin A ("COMPOUND H")

A mixture of 575 mg of Compound G, 50 mg of sodium aside and 2 mg of dimethylsulphoxide were stirred for 2 hours at 100° C, under an atmosphere of nitrogen. The mixture was allowed to cool, and cold water was then added to it. The precipitate which formed was collected by filtration and dissolved in chloroform. The chloroform solution was washed with water and dried over anhydrous magnesium sulphate. The solvent was removed, giving 500 mg of crude "Compound H".

This crude product was adsorbed on a column of 7 g of silica gel, which was eluted with chloroform containing 0.5% by volume of methanol. The solvent was removed from the eluate, giving 429 mg of the pure desired Compound H. When further precipitated with a mixture of ethyl acetate and hexane, the pure product was obtained in the form of a powder melting at 80°–101° C.
$[\alpha]_D^{25} = -1.8°$ (C = 2.8, CHCl$_3$).
IR spectrum in Nujol (Trade Mark): $\nu = 2100$ (sharp absorption due to azide).
Elemental analysis: Calculated for $C_{61}H_{74}O_{26}N_8S_2$: C, 52.34%; H, 5.33%; N, 8.01%; S, 4.58%; Found: C, 52.49%; H, 5.18%; N, 8.13%; S, 4.76%.

(8)
5''-Azido-tetra-N-benzyloxycarbonyl-3',4'-5''-trideoxy-3'-enobutirosin ("Compound I")

A mixture of 3.77 g of Compound H, 25 g of sodium iodide and dimethylformamide was stirred with heating for 2 hours at 130° C (bath temperature). The mixture was allowed to cool, then chloroform was added, and the precipitate which formed was filtered off. The filtrate was washed with 10% aqueous sodium thiosulphate solution and then with saturated aqueous sodium hydroxide solution, and dired over magnesium sulphate. The solvent was removed, leaving 2.8 g of a dark brown powder.

This powder was dissolved in 15 ml of methanol, 0.7 ml of 2N methanolic sodium methoxide solution was added, and the resulting solution was stirred for 1 hour at room temperature. The solution was then neutralized with acetic acid and concentrated under reduced pressure. The residue was adsorbed on a column of 30 g of silica gel. The column was washed with chloroform to remove impurities, and then eluted successively with 400 ml of chloroform containing 2% methanol, 400 ml of chloroform containing 3% methanol and 200 ml of chloroform containing 4% methanol (all percentages of volume). The eluates with the chloroform containing 3% and 4% methanol were analysed by thin-layer chromatography on silica gel (developed with a 1:9 by volume mixture of methanol and chloroform), and the fractions containing a chromatographically pure product were collected. The solvent was distilled off from these fractions of eluate, giving 685 mg of the pure "Compound I" (i.e. the starting material used in the foregoing Example) in the form of a powder.
$[\alpha]_D^{20} = -29.2°$ (C = 1.2, MeOH)
NMR (60MHZ, CDCl$_3$): δ = 5.58 (s, protons on 3' and 4' carbons)
Elemental analysis: Calculated for $C_{53}H_{62}O_{17}N_8 \cdot H_2O$: C, 57.81%; H, 5.86%; N, 10.18%; Found: C, 58.09%; H, 5.52%; N, 9.89%.

We Claim:
1. Compounds having the formula (I):

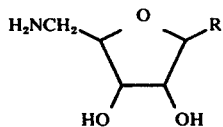

wherein R is a radical of formula (II):

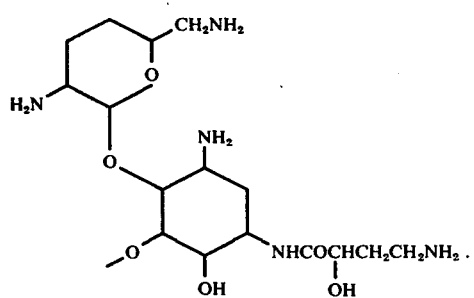

2. Acid addition salts of a pharmaceutically acceptable acid and a compound of formula (I):

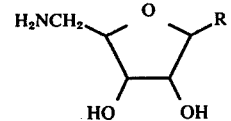

wherein R is a radical of formula (II):

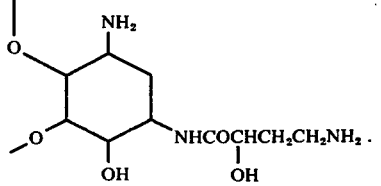

3. Acid addition salts as claimed in claim 2, wherein said acid is selected from the group consisting of: hydrochloric, hydrobromic, sulphuric, phosphoric, carbonic, acetic, succinic, citric, maleic and malic acid.

4. 5''-Amino-3',4',5''-trideoxybutirosin A and pharmaceutically acceptable acid addition salts thereof.

5. 5''-Amino-3',4',5''-trideoxybutirosin A carbonate.

* * * * *

UNITED STATES PATENT OFFICE
CERTIFICATE OF CORRECTION

Patent No. __4,006,133__  Dated __February 1, 1977__

Inventor(s) __Eiji Ohki et al__

It is certified that error appears in the above-identified patent and that said Letters Patent are hereby corrected as shown below:

In the heading of the Patent [30] should read as follows:

--[30]  Foreign Application Priority Data
Oct. 25, 1973    Japan........48-120324 --.

Signed and Sealed this

Tenth Day of May 1977

[SEAL]

Attest:

RUTH C. MASON
*Attesting Officer*

C. MARSHALL DANN
*Commissioner of Patents and Trademarks*